United States Patent [19]
Mahlmann

[11] Patent Number: 6,068,477
[45] Date of Patent: May 30, 2000

[54] FOAM-CUSHIONED ASPIRATOR

[76] Inventor: Lee A. Mahlmann, 4411 Ave. N, Rosenberg, Tex. 77471

[21] Appl. No.: 09/347,395

[22] Filed: Jul. 6, 1999

Related U.S. Application Data

[60] Provisional application No. 60/091,832, Jul. 5, 1998.

[51] Int. Cl.⁷ .............................. A61C 17/06; A61C 5/14
[52] U.S. Cl. ................... 433/96; 433/95; 433/94; 433/136
[58] Field of Search ................... 433/96, 95, 94, 433/93, 91, 136; 604/115

[56] References Cited

U.S. PATENT DOCUMENTS

| | | | |
|---|---|---|---|
| 15,344 | 7/1912 | Hallam | 433/96 |
| Re. 24,898 | 11/1960 | Cohn . | |
| 2,595,666 | 5/1952 | Hutson | 433/96 |
| 2,637,106 | 5/1953 | Otis . | |
| 3,324,855 | 6/1967 | Heimlich . | |
| 3,758,950 | 9/1973 | Krouzian . | |
| 3,785,380 | 1/1974 | Brumfield | 128/276 |
| 4,233,025 | 11/1980 | Larson et al. . | |
| 4,259,067 | 3/1981 | Nelson | 433/93 |
| 5,066,228 | 11/1991 | Doundoulakis et al. | 433/91 |
| 5,094,616 | 3/1992 | Levenson | 433/93 |
| 5,151,094 | 9/1992 | Hanifl . | |
| 5,762,496 | 6/1998 | Albertsson et al. | 433/93 |
| 5,924,866 | 7/1999 | Eldreth | 433/93 |

FOREIGN PATENT DOCUMENTS

| | | | |
|---|---|---|---|
| 3734762 | 5/1989 | Germany | 433/95 |
| 248708 | 12/1963 | Sweden | 433/96 |
| 0003470 | 8/1979 | Sweden | 433/96 |
| 7900546 | 8/1979 | Sweden | 433/96 |

*Primary Examiner*—John J. Wilson
*Assistant Examiner*—Rolyn Kieu Doan
*Attorney, Agent, or Firm*—James L. Jackson; Mayor, Day, Caldwell & Keeton, L.L.P.

[57] ABSTRACT

A disposable cushioned aspirator which forms part of a dental or medical aspirating system. The disposable cushioned aspirator appliance described herein is intended principally to be used in dental procedures where bodily fluids and rinse water is evacuated from a patient's mouth, but the invention has application in medical procedures and various other applications as well. An elongate tubular element having a patient end and a connection end is exteriorly lined with a layer of soft cushioning material such as a porous foam material to protect the soft tissues in and around the mouth of a patient. The elongate tubular aspirator is capable of being manually bent from an initially straight configuration to a curved or other desired configuration and is provided with a structural member extending along its length and being pliable to permit bending and yet of sufficient structural integrity to maintain the aspirator in the desired configuration during use. The structural member is preferably a wire element which is embedded within or attached to the elongate tubular element.

19 Claims, 2 Drawing Sheets

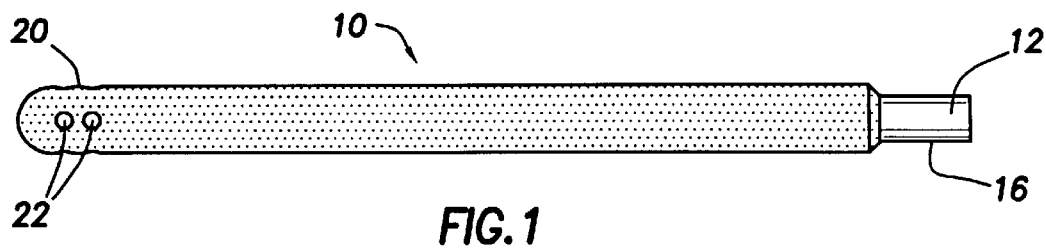
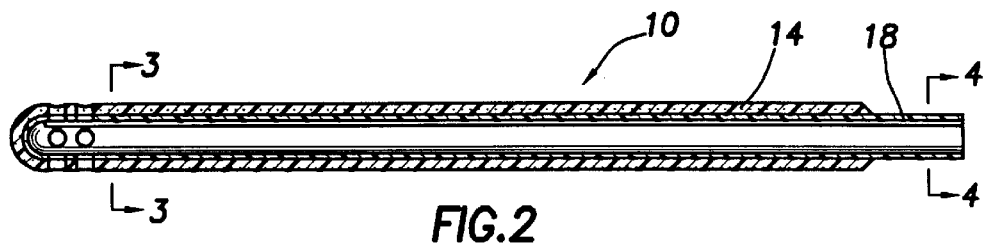
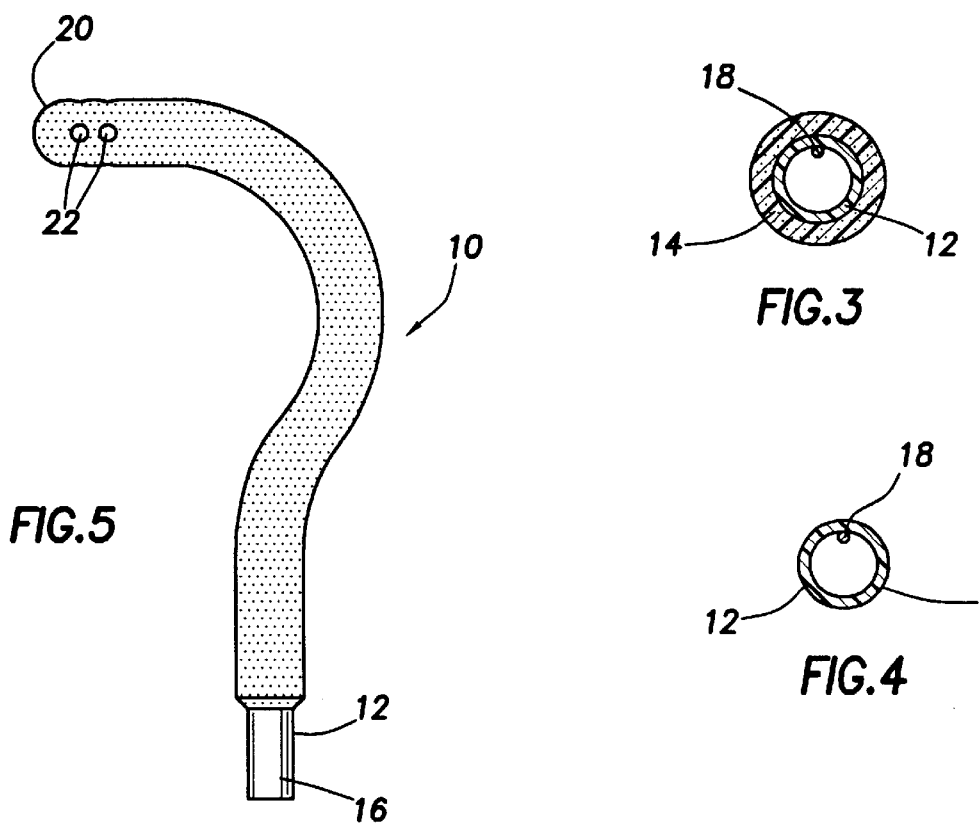

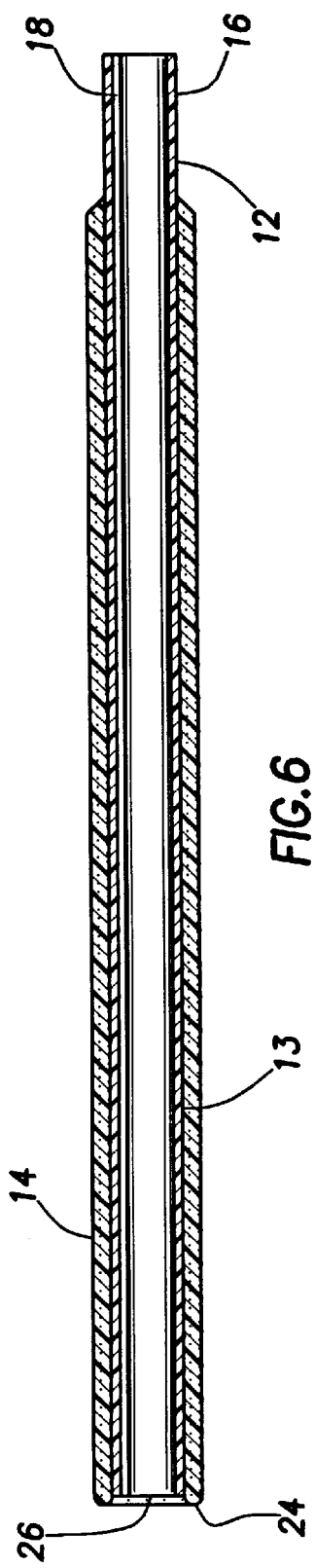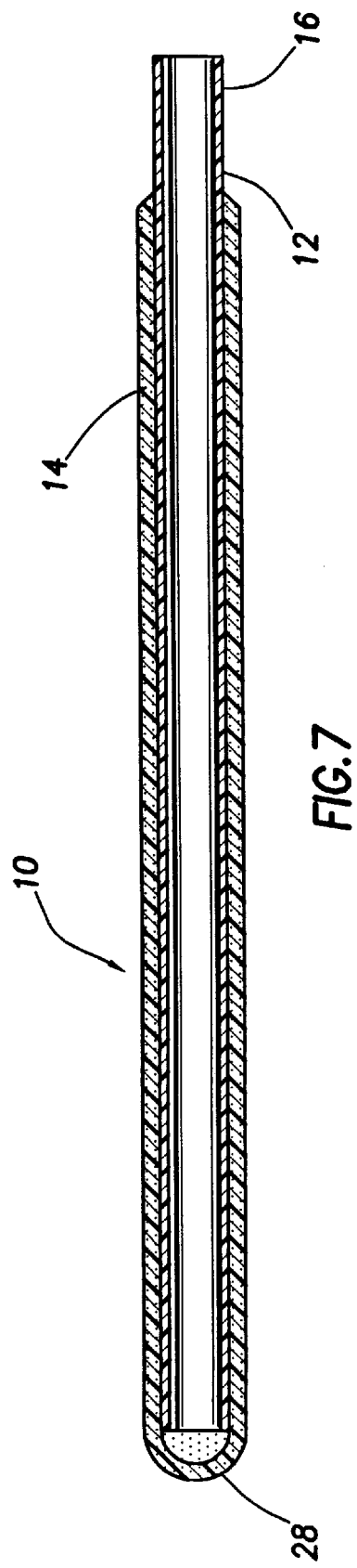

FOAM-CUSHIONED ASPIRATOR

Applicant hereby claims the benefit of U.S. Provisional Application Ser. No. 60/091,832 filed on Jul. 6, 1998 by Lee A. Mahlmann, and entitled Foam Tip Aspirator, which is incorporated herein by reference for all purposes.

BACKGROUND OF THE INVENTION

1. Field of the Invention

This invention relates generally to aspirators for use by medical and dental practitioners for removal of body fluid from the immediate region of a medical or dental procedure. More particularly, the present invention concerns a foam-cushioned aspirator for aspiration of fluids, including body fluids such as blood, saliva, rinse water and the like, as well as other fluids or fluid like materials from a region of interest, while substantially eliminating the potential for aspiration of soft flaccid tissues into aspirator openings. Even more particularly, the present invention concerns the provision of a foam covered aspirator which presents a soft, cushioned aspirator surface for contact with body tissues to prevent damage to body tissues and to promote the general comfort of the patient.

2. Description of the Prior Art

The tissue inside the human mouth and lip area around the mouth is very sensitive. In most dental procedures, a saliva ejector is used to dry the mouth so the procedure can be carried out without the inconvenience of a wet field. The problem with most saliva ejectors is that they are made of a hard, non-forgiving plastic or metal. When positioned under the tongue or labial vestibule, the saliva ejector aspirates saliva, blood, and unfortunately the soft, flacid tissues. Once the tissue is aspirated into the holes or slits of the saliva ejector a blood blister is created. When the aspirator is removed from the mouth it is very painful to the patient and a "blood blister" remains.

Not only does the hard plastic or metal aspirator cause discomfort inside the mouth but often pinches the lower lip against the lower teeth. This can cause pain in the lip and can actually bruise the lip.

The discomfort that a hard aspirator can cause during a dental procedure can greatly affect the outcome. An uncomfortable patient is not as cooperative as a comfortable one. The end result can be less than ideal.

The Foam-cushioned Aspirator I have designed in multiple sizes and tip designs can eliminate the problems caused by a hard plastic or metal aspirator. The foam does not allow the aspirator to impinge, aspirate, or bruise any tissue in or around the oral cavity. This design is not only ideal for use in dentistry but can also be utilized in many medical applications. It is gentle to all soft tissues it contacts.

SUMMARY OF THE INVENTION

This invention was designed to be the beginning piece of a dental or medical aspirating system. It was designed, for example, to be inserted into a patient's mouth to remove collected saliva/water by means of suction. The appliance is attached to a remote central vacuum unit by way of a flexible tube having a conventional vacuum line connection for medical and dental operators. The present invention is unique in that it has a skeletal structure made up of a plastic tube in which a wire is embedded to allow the aspirator to be bent or otherwise formed to a specific shape for a specific dental or medical procedure. The skeletal plastic tube is covered almost completely by a non-toxic, open cell, foam material that protects not only the soft tissue within the mouth but all tissues around the mouth. With other types of aspirators, only the tips that contact the oral tissues have foam. This device has cushioning foam it's full length except an end connection part that fits to the central vacuum tubing by means of a conventional medical/dental vacuum line connection. Thus the cushioning effect of the aspirator of this invention protects not only the soft tissue within the mouth but also the teeth and lips.

The actual design of the aspirator is very simple. It consists of a plastic tube, strong enough to withstand strong suction. It has a wire imbedded in it, the full length, to allow it to be formed to a specific shape to fit different dental or medical procedures. The tube is surrounded by a soft foam that covers all but a small section of the tube that connects to the central vacuum tubing.

BRIEF DESCRIPTION OF THE DRAWINGS

So that the manner in which the above recited features, advantages and objects of the present invention are attained and can be understood in detail, a more particular description of the invention, briefly summarized above, may be had by reference to the preferred embodiment thereof which is illustrated in the appended drawings, which drawings are incorporated as a part hereof.

It is to be noted however, that the appended drawings illustrate only a typical embodiment of this invention and are therefore not to be considered limiting of its scope, for the invention may admit to other equally effective embodiments.

In The Drawings

FIG. 1 is a side view of a foam-cushioned aspirator representing the preferred embodiment of the present invention;

FIG. 2 is a longitudinal sectional view of the foam-cushioned aspirator of FIG. 1;

FIG. 3 is a sectional view taken along line 3—3 of FIG. 2;

FIG. 4 is a sectional view taken along line 4—4 of FIG. 2 and showing the relationships of the flexible tube element and the structural wire;

FIG. 5 is an elevational view showing the foam-cushioned aspirator of the present invention being bent to a curved form particularly for dental use;

FIG. 6 is a longitudinal sectional view of an alternative embodiment of the present invention, showing the patient end thereof having an open tip; and FIG. 7 is a longitudinal sectional view of another alternative embodiment of the present invention, showing a closed aspirator tip at the patient end thereof.

DETAILED DESCRIPTION OF PREFERRED EMBODIMENT

Referring now to the drawings and first to FIG. 1, a disposable foam-cushioned aspirator representing the preferred embodiment of the present invention is shown generally at 10. The foam-cushioned aspirator 10 of FIG. 1 consists of an elongated hollow plastic tube 12 having substantially its entire external surface 13 covered by a layer of soft polymer foam 14. The only portion of the elongate tubular element 12 which is exposed is a connector end section 16 which enables attachment of the foam-cushioned aspirator 10 to the usual flexible tube of a central vacuum pump or system (not shown) through the use of conventional flexible tubing and connectors. The connector end section 16 of the aspirator can range in size for example from about 10 mm to about 35 mm. Within the hollow plastic tube 12 is an embedded stainless steel wire 18 which is soft and pliable and allows for the aspirator to be bent to conform to a specific configuration for use in a dental or medical procedure (FIG. 5). The wire size would be such that it would be large enough in diameter to perform its necessary function, but at the same time not too large as to inhibit the suction capacity of the tubing. The structural integrity of the stainless steel wire is sufficient to permit the foam-cushioned aspirator to be manually bend to a desired configuration and to maintain the desired configuration during use. In some applications where the aspirator tube does not need to be bendable the wire can be left out and the hollow plastic tube would stand alone. The hollow plastic tubing 12 can have an inside diameter ranging from about 3 mm to whatever size meets the need. The foam 14 covering the hollow plastic tubing can range in thickness from about 1 mm to whatever thickness is needed to meet the cushioned effect that is desired. The normal foam thickness range would be from about 1 mm to about 3 mm. The overall length of the foam-cushioned aspirator can be variable depending on dental or medical procedure it is being used for. For a dental procedure the average length would range from for example from about 90 mm to about 150 mm.

The patient end 20 of the aspirator, as shown in FIG. 1, FIG. 6 and FIG. 7, through which saliva/blood/water and debris is aspirated into the hollow plastic tube and foam is shown in three different forms. FIG. 1 shows the tip with multiple liquid aspiration holes 22 through the foam ranging in size from 0.5 to 2 mm in diameter. FIG. 6 represents an alternative embodiment of the present invention which shows the aspirator with an open tip 24 to allow aspiration of not only saliva, water, and blood, but also large debris particles. As noted in FIG. 6, the foam covering 14 of the aspirator extends from about 2 mm to about 4 mm past the patient end 26 of the hollow plastic tube 12 to provide for a cushioned effect when the patient end of the foam-cushioned aspirator is moved into engagement with soft or flaccid tissue of the patient. This feature effectively prevents damage to the soft tissue of the patient if the tissue is forced into the aspirator opening under the influence of vacuum.

FIG. 7 is a further alternative embodiment of the present invention which shows the foam-cushioned aspirator with a closed foam tip 28 which requires that suction be applied through the porous foam cushioning material. The foam in this application would need to be porous enough to allow for suction to occur and to allow typically occurring liquid material to flow through the foam material and into the aspirator tube. Polyurethane foam would best suit this purpose and comes in two types; polyether based and polyester based. The polyether based foam would be best because it has greater flexibility and allows for greater suction/air flow rate.

The aspirator described is made up of both solid plastic and plastic foam. Both parts can be made from non-toxic materials such as polyurethane, rubber, latex, polyethylene, polyvinyl chloride, or vinyl polymides. The materials used to make these parts would be chosen and dimensioned to meet specific operative characteristics.

The foam covering the hollow plastic tube could, if necessary, be glued or bonded. The foam material will most practically take the form of a sleeve of foam material which is positioned over the external surface of the elongate flexible aspirator tube. In most cases, the tubular foam covering would fit tight enough so glue or bonding material would not be necessary. If glue or bonding material is used to secure the polymer foam material to the elongate flexible tube, it should be of a non-toxic, water insoluable type. It is also envisioned that, according to some manufacturing processes, and within the spirit and scope of the present invention, the polymer foam material could be applied to the elongate flexible tube in an uncured state and permitted to cure in place.

In view of the foregoing it is evident that the present invention is one well adapted to attain all of the objects and features hereinabove set forth, together with other objects and features which are inherent in the apparatus disclosed herein.

As will be readily apparent to those skilled in the art, the present invention may easily be produced in other specific forms without departing from its spirit or essential characteristics. The present embodiment is, therefore, to be considered as merely illustrative and not restrictive, the scope of the invention being indicated by the claims rather than the foregoing description, and all changes which come within the meaning and range of equivalence of the claims are therefore intended to be embraced therein.

I claim:

1. A cushioned aspirator, comprising:
   (a) an elongate tubular element defining an internal flow passage and having a connection end and a patient end and having sufficient flexibility for bending thereof to a desired configuration, said connection end being adapted for connection to a conventional aspirator suction connection fitting, said patient end defining at least one aspirator opening through which fluid is aspirated to said internal flow passage;
   (b) a covering of cushioning material extending from said connection end to said patient end and being of sufficient thickness to present a cushioned aspirator surface for contact with the patient, said covering of cushioning material substantially enclosing said patient end of said elongate tubular element and extending along a major portion of said elongate tubular element and defining fluid a plurality of flow passages permitting aspiration of fluid therethrough to said at least one aspirator opening; and
   (c) a length of structural material being fixed along its length to said elongate tubular element and extending longitudinally along substantially the entire length of said elongate tubular element, said length of structural material being sufficiently pliable to permit bending of said cushioned aspirator to a desired configuration and of sufficient structural integrity to maintain said cushioned aspirator at the desired configuration.

2. The cushioned aspirator of claim 1, comprising:
   said length of structural material being composed of wire.

3. The cushioned aspirator of claim 1, comprising:
   (a) said elongate tubular element defining a wall structure forming said internal flow passage, and
   (b) said length of structural material being a length of wire embedded within said elongate tubular element.

4. The cushioned aspirator of claim 1, comprising:
   (a) said elongate tubular element being composed of a polymer material and defining a tubular wall structure having an inner surface forming said internal flow passage; and
   (b) said length of structural material being composed of wire and being embedded within said tubular wall structure polymer material of said elongate tubular element and extending substantially the entire length of said elongate tubular element.

5. The cushioned aspirator of claim 1, comprising:
(a) said elongate tubular element having a tubular wall structure defining an inner surface; and
(b) said length of structural material being fixed along its length to said inner surface of said tubular wall structure of said elongate tubular element and extending the entire length of said elongate tubular element and intersecting said connection end and said patient end.

6. The cushioned aspirator of claim 1, comprising:
(a) said elongate tubular element having a tubular wall structure defining an exterior surface; and
(b) said covering of cushioning material being a tubular foam member being disposed about and in contact along its length with said exterior surface, enclosing said patient end of said elongate tubular element and extending to said connection end of said elongate tubular element.

7. The cushioned aspirator of claim 1, comprising:
(a) said elongate tubular element defining an exterior surface;
(b) said covering of cushioning material being in the form of an elongate porous tubular foam member being disposed about said exterior surface of said elongate tubular element; and
(c) said elongate tubular foam member being fixed to said exterior surface of said elongate tubular element.

8. The cushioned aspirator of claim 1, comprising:
(a) said at least one aspirator opening being a plurality of first aspirator openings defined in said elongate tubular element; and
(b) said covering of cushioning material being a polymer foam sleeve having a rounded end portion extending beyond and enclosing said patient end of said elongate tubular element and extending along said elongate tubular element to said connection end and defining a plurality of second aspirator openings disposed in registry with said first aspirator openings and providing for cushioning of patient tissues along substantially the entire length of said elongate tubular element, at said rounded end portion of said covering of polymer foam material and at said second aspirator openings.

9. The cushioned aspirator of claim 1, comprising:
(a) said at least one aspirator opening being a plurality of aspirator openings defined in said elongate tubular element; and
(b) said covering of cushioning material being a covering of porous foam material enclosing said patient end of said elongate tubular element and defining a multiplicity of pores through which fluid is caused to flow through said porous foam material and through said plurality of aspirator openings, said covering of porous foam material about said patient end of said elongate tubular and element providing for cushioning of patient tissues at said plurality of aspirator openings.

10. The cushioned aspirator of claim 1, comprising:
(a) said at least one aspirator opening being a single aspirator opening defined by said patient end of said elongate tubular element; and
(b) said covering of cushioning material extending beyond and enclosing said patient end of said elongate tubular element and defining a cushioning material aspirator opening in communication with said at least one aspirator opening and providing for cushioning of patient tissue when said patient end of said cushioned aspirator is caused to contact patient tissue.

11. A cushioned aspirator, comprising:
(a) an elongate tubular element having a connection end and a patient end and having sufficient flexibility for bending thereof to a desired configuration, said connection end being adapted for connection to a conventional aspirator suction connection fitting, said patient end defining at least one aspirator opening through which fluid is aspirated; and
(b) a covering of polymer foam material extending from said connection end to said patient end and having a rounded extremity extending beyond and being disposed about and enclosing said patient end and being of sufficient thickness to present a cushioned aspirator surface for contact with the patient, said covering of polymer foam material about said patient end of said elongate tubular element defining fluid flow passages permitting aspiration of fluid there through.

12. The cushioned aspirator of claim 11, comprising:
(a) said elongate tubular element defining a tubular wall structure, and
(b) a length of structural material being disposed within said tubular wall structure of said elongate tubular element and extending longitudinally thereof and substantially along the entire length thereof, said length of structural material being sufficiently pliable to permit bending of said cushioned aspirator to a desired configuration and of sufficient structural integrity to maintain said cushioned aspirator at the desired configuration.

13. The cushioned aspirator of claim 12, comprising:
said length of structural material being composed of wire.

14. The cushioned aspirator of claim 12, comprising:
said length of structural material being embedded within said tubular wall structure of said elongate tubular element.

15. The cushioned aspirator of claim 11, comprising:
(a) said elongate tubular element being composed of a polymer material and said tubular wall structure defining an inner surface forming a flow passage from said patient end to said connection end; and
(b) a length of wire material being embedded within said polymer material of said tubular wall structure of said elongate tubular element and extending substantially the entire length of said elongate tubular element.

16. The cushioned aspirator of claim 11, comprising:
(a) said tubular wall structure of said elongate tubular element defining an inner surface having a flow passage from said patient end to said connection end; and
(b) a length of structural material being fixed along the length thereof to said inner surface of said elongate tubular element and extending substantially the entire length of said flow passage of said elongate tubular element.

17. The cushioned aspirator of claim 11, comprising:
(a) said elongate tubular element having a tubular wall structure defining an exterior surface; and
(b) said covering of polymer foam cushioning material being a tubular foam member being disposed about and being fixed to said exterior surface of said elongate tubular element;
(d) said at least one aspirator opening being a plurality of first aspirator openings defined in said elongate tubular element; and (e) said covering of cushioning material having a rounded closed end extending beyond and enclosing said patient end of said elongate tubular element and defining a plurality of second aspirator openings disposed in registry with said first aspirator openings and providing for cushioning of patient tissues.

18. The cushioned aspirator of claim 11, comprising:

(a) said at least one aspirator opening being a plurality of aspirator openings defined in said elongate tubular element; and (b) said covering of cushioning material being a covering of porous foam material enclosing said patient end of said elongate tubular element and defining a multiplicity of pores through which fluid is caused to flow through said porous foam material and through said plurality of aspirator openings, said covering of porous foam material about said patient end of said elongate tubular and element providing for cushioning of patient tissues at said plurality of aspirator openings.

19. The cushioned aspirator of claim 11, comprising:

(a) said at least one aspirator opening being a single aspirator opening defined by said patient end of said elongate tubular element; and (b) said covering of cushioning material defining a rounded closed end extending beyond said patient end of said elongate tubular element and defining a cushioning material aspirator opening and providing for cushioning of patient tissue when said patient end of said cushioned aspirator is caused to contact patient tissue.

* * * * *